(12) United States Patent  
Safar et al.

(10) Patent No.: US 7,815,866 B2
(45) Date of Patent: Oct. 19, 2010

(54) APPARATUS AND METHOD FOR HANDLING FLUIDS FOR ANALYSIS

(75) Inventors: Scott G. Safar, Burlington, WI (US); Stephen L. Herchenbach, Antioch, IL (US); Chadwick M. Dunn, Chicago, IL (US); Charles M. Galitz, Kenosha, WI (US); Julius J. Toth, Wauconda, IL (US); Ronald E. Kukla, Wheeling, IL (US); Michael G. Lowery, Wildwood, IL (US); Eric B. Shain, Glencoe, IL (US)

(73) Assignee: Abbott Laboratories, Inc., Abbott Park, IL (US)

( * ) Notice: Subject to any disclaimer, the term of this patent is extended or adjusted under 35 U.S.C. 154(b) by 0 days.

(21) Appl. No.: 12/486,074

(22) Filed: Jun. 17, 2009

(65) Prior Publication Data

US 2009/0252652 A1 Oct. 8, 2009

Related U.S. Application Data

(62) Division of application No. 10/865,207, filed on Jun. 10, 2004.

(60) Provisional application No. 60/479,710, filed on Jun. 19, 2003.

(51) Int. Cl.
*B01L 9/00* (2006.01)
*B01L 99/00* (2010.01)

(52) U.S. Cl. .................. 422/104; 422/101; 422/102

(58) Field of Classification Search ............... 422/101, 422/102, 104

See application file for complete search history.

(56) References Cited

U.S. PATENT DOCUMENTS 3,985,649 A 10/1976 Eddelman
4,041,995 A 8/1977 Columbus (Continued)

FOREIGN PATENT DOCUMENTS

DE 19828995 2/1999

(Continued)

OTHER PUBLICATIONS

PCT Search Report (Aug. 19, 2005).

(Continued)

*Primary Examiner*—Walter D Griffin
*Assistant Examiner*—Lessanework Seifu
(74) *Attorney, Agent, or Firm*—David L. Weinstein (57) ABSTRACT

A reaction vessel with a bottom drain opening supporting a selected unpressured head of fluid by the surface tension of the fluid. A device processing zone includes a support for spaced rows of reaction vessels, passages communicating with their drain openings of supported vessels, and a pressure source for selectively draining fluid through the drain openings. Generally horizontal bar magnets are supported for selected vertical movement between the vessel rows. A dispensing head has X discharge openings selectively positionable over X selected reaction vessels. A metering pump mechanism selectively meters X a selected quantity of fluid a bulk supply (where X is at least four), and selectively pumps the metered selected quantities through the drain openings to the selected reaction vessels. Methods of drawing fluid from the vessels using the pressure source, and moving the magnets to form a pellet of analyte are also included.

6 Claims, 7 Drawing Sheets

U.S. PATENT DOCUMENTS

| | | |
|---|---|---|
| 4,642,220 A | 2/1987 | Bjorkman |
| 4,895,650 A | 1/1990 | Wang |
| 4,948,564 A | 8/1990 | Root et al. |
| 5,306,510 A | 4/1994 | Meltzer |
| 5,368,729 A | 11/1994 | Stefkovich et al. |
| 5,976,369 A | 11/1999 | Howe et al. |
| 6,001,311 A | 12/1999 | Brennan |
| 6,063,282 A | 5/2000 | Moulton |
| 6,117,398 A | 9/2000 | Bienhaus et al. |
| 6,149,869 A * | 11/2000 | Antonenko et al. ........... 506/40 |
| 6,183,645 B1 | 2/2001 | DeWitt |
| 6,231,760 B1 | 5/2001 | Siddiqi |
| 6,413,780 B1 | 7/2002 | Bach et al. |
| 6,485,690 B1 | 11/2002 | Pfost et al. |
| 2001/0019845 A1 | 9/2001 | Bienert et al. |
| 2002/0127721 A1 | 9/2002 | Davidson et al. |
| 2002/0137194 A1 | 9/2002 | Ammann et al. |
| 2003/0017349 A1 | 1/2003 | Brown et al. |
| 2003/0109060 A1 | 6/2003 | Cook et al. |
| 2004/0005714 A1 | 1/2004 | Safar et al. |

FOREIGN PATENT DOCUMENTS

| | | |
|---|---|---|
| EP | 0508530 A1 | 10/1992 |
| EP | 1025902 B1 | 8/2000 |
| EP | 1065001 A1 | 1/2001 |
| EP | 1103304 A2 | 5/2004 |
| EP | 1441225 A1 | 7/2004 |
| FR | 2091793 | 1/1972 |
| WO | 9714041 A1 | 4/1997 |
| WO | 0066214 A1 | 11/2000 |
| WO | 01/70402 A2 | 9/2001 |
| WO | 03016832 A2 | 2/2003 |

OTHER PUBLICATIONS

Extended European Search Report (Jul. 3, 2006).
Partial European Search Report (Jun. 23, 2006).
Extended European Search Report (Oct. 2, 2006).

* cited by examiner

APPARATUS AND METHOD FOR HANDLING FLUIDS FOR ANALYSIS

CROSS REFERENCE TO RELATED APPLICATION(S)

This application is a divisional application claiming priority from U.S. patent application Ser. No. 10/865,207, filed Jun. 10, 2004, which claims priority from U.S. Provisional Application Ser. No. 60/479,710, filed Jun. 19, 2003.

TECHNICAL FIELD

The present invention is directed toward testing of specimens, and particularly toward an apparatus and method for processing specimens during testing, including adding fluids such as reagents during the processing of specimens.

BACKGROUND OF THE INVENTION AND TECHNICAL PROBLEMS POSED BY THE PRIOR ART

Testing sample biological specimens is commonly done, for example, to check for the presence of an item of interest, which item may be or include all or portions of a specific region of DNA, RNA, or fragments thereof, complements, peptides, polypeptides, enzymes, prions, proteins, messenger RNA, transfer RNA, mitochondrial RNA or DNA, antibodies, antigens, allergens, parts of biological entities such as cells, virons or the like, surface proteins, or functional equivalents of the above, etc. Specimens such as a patient's body fluids (e.g., serum, whole blood, urine, swabs, plasma, cerebral-spinal fluid, lymph fluids, tissue solids) can be analyzed using a number of different tests to provide information about a patient's health.

In such testing, it is imperative that the specimens be handled in a manner which prevents contaminants from being introduced to the specimens, whether from the outside environment or between specimens. For example, where the HIV virus from one specimen is inadvertently allowed to contaminate the specimen of a different patient, the resulting false positive test result could potentially have catastrophic psychological effect on the patient, even should subsequent testing later discover the error. Moreover, since such testing is highly sensitive, even the smallest amounts of contamination can cause erroneous test results. Simply put, it is imperative that the specimens be properly handled.

In such sophisticated testing, it is also imperative that the various reagents which may be used in the testing be properly handled as well, not only to avoid contaminants but also to ensure that the proper reagent in proper quantities is used at appropriate times.

Commonly, such testing is accomplished using automated devices which handle multiple specimens and fluids (typically, reagents). Such automated devices typically will use sets of pipettes to move various fluids between their original containers (usually receptacles such as open topped tubes) and containers in which the specimens are to be processed. For example, a set of 8 specimens may be contained in 8 tubes or other receptacles loaded in a rack on the device, and a head carrying 8 pipettes will, through programmed motion, move the pipettes into those 8 tubes, where a vacuum will be applied to extract a selected amount of each specimen from its tube into the pipettes. The head will then retract the pipettes from the tubes and move to another set of tubes located at a processing station, depositing the extracted amounts of each specimen from the pipettes into sets of testing tubes.

In such automated devices, racks or trays of multiple tubes are usually moved from one station to the next for different stages of processing. For example, a heating element may be provided at one station, and a magnetic element introducing a magnetic field in the tubes may be provided at another station. Further, in such situations, multiple trays of multiple tubes may be actively processed in series and simultaneously at different stations. However, such processing can result in resource contention, where one rack of tubes is delayed from being placed at a station while another rack of tubes completes its processing at that station when, as is commonly the case, the processing time at one station is different than the processing time at another station. For example, a tray of tubes which have completed processing at one station may be delayed from being processed at the next station until another tray of tubes at that next station has completed its processing there. Like a chain which is no stronger than its weakest link, such an automated device will provide an overall processing time which is a function of the processing time at the slowest station. Of course, a slow overall processing time can reduce the amount of tests which are performed during a given day, and thereby either delay the completion of tests or require significant additional investment of capital for additional devices to allow for a desired testing capacity level.

At the processing stations of such automated devices, the specimens are variously handled according to the purpose of the testing (e.g., incubated, prepared, lysed, eluted, etc.). For example, the specimens may be prepared for analyzing, as for example by separating DNA or RNA from the specimen. The specimens may also or alternatively be analyzed. Commonly, such processes involve the addition of various fluids (typically reagents) to the specimen in each tube. For example, in a first step, a reagent may be added to each of the tubes to wash the specimens, and second and third (and more) reagents may be added to the specimens in the course of carrying out other processes to, for example, unbind and/or separate the DNA or RNA of interest so that it may be extracted from the specimen in each tube for subsequent testing. Similar processes, in which the same or different reagents are added to and/or extracted from the tubes, may also occur after the specimen has been prepared as part of analyzing the prepared specimens.

In some processes, magnetic fields have been used to assist in separating analytes of interest from the fluid in the tubes. For example, analytes of interest have been bound to magnetic particles within a reagent and a magnetic field applied to pull the particles and bound analyte to one side of the tube, whereby the reagent may be drawn out of the tube to leave a concentration of the analyte therein. Where it has been necessary to adjust the magnetic field within the tubes (e.g., in order to change the location where the analytes are to be drawn), the tubes have been moved in order to accomplish the desired orientation of the magnetic field in the tubes.

The handling of the reagents and other fluids with automated devices such as described above can be problematic. Though the reagents may be automatically moved from receptacles to the specimen containing tubes in the processing station by use of the head and pipettes such as noted, it is in the first instance necessary to load the appropriate reagent into the appropriate receptacle on the device in order to ensure that the head and pipettes are adding the appropriate reagent to the appropriate specimen containing tube at the appropriate time in the process. Further, it should be recognized that it is necessary for the receptacles to be readily cleaned, whether to remove possible contaminants or to permit use of different fluids in connection with different processes. As a result of such requirements, the receptacles are typically readily removable from the apparatus for such action.

Heretofore, loading the appropriate reagent into the appropriate receptacle has been accomplished in several different ways. In one such procedure, the individual who is controlling the device manually measures and adds the reagents to receptacles, and then places those receptacles on the device. In another such procedure, the loading of reagents is automatically accomplished by the device itself, which uses some transfer apparatus (such as a head and pipette(s) as previously described) to move the reagents from bulk supplies of the reagents provided with the device.

Removing reagents from tubes is similarly accomplished, such as by use of a head which positions pipettes in the tube and vacuum draws the fluid from the tubes into the pipettes. Such a process can be time consuming, and tie up the head from other uses, particularly if prevention of contamination between tubes makes it necessary to use a new pipette with each tube. In such cases, it may be necessary to repetitively move the head to discharge, discard and pick up new pipettes every time fluid is drawn from tubes (e.g., a head carrying eight pipettes may have to be cycled six times when used with a tray of 48 tubes, where each cycle requires discharging and discarding used pipettes, and picking up new pipettes). Of course, in such situations, multiple pipettes will be consumed at some cost. U.S. Pat. No. 6,117,398 alternatively discloses drawing fluid from the bottom of a sample vessel, wherein a valve is situated between every sample processing vessel and the waste container.

The present invention is directed to overcoming one or more of the problems as set forth above.

SUMMARY OF THE INVENTION

In one aspect of the present invention, a reaction vessel for testing an analyte in a fluid is provided. The vessel has an open top and a drain opening in its bottom, with the drain opening being adapted to support a selected head of fluid and to drain fluid therethrough when a selected pressure differential exists between the top of the fluid and the bottom of the vessel.

In one form of this aspect of the invention, the surface tension of the fluid supports the selected head of fluid when the pressure differential between the top of the fluid and the bottom of the vessel is less than the selected pressure differential.

In another form of this aspect of the invention, a hydrophobic frit is associated with the drain opening.

In another form of this aspect of the invention, the drain opening permits draining of the fluid only when the relative pressure between the top of the fluid and the drain opening is at least a selected amount.

In still another form, a non-wettable surface is provided around the drain opening on the outside of the vessel.

In yet another form, a drain opening protrusion extends beyond the bottom surface of the vessel.

In another aspect of the present invention, a processing zone for a specimen handling device is provided, including a support for a plurality of reaction vessels having drain openings in their bottoms, passages adapted to communicate with the bottom drain openings of supported reaction vessels, and a source of air at non-atmospheric pressure adapted to selectively drain fluid through the drain openings in supported reaction vessels. The drain openings are adapted to support a selected head of fluid in the vessels.

In one form of this aspect of the invention, the source of air at non-atmospheric pressure is a vacuum source for drawing a vacuum in the passages.

In another form of this aspect of the invention, a heater is provided for heating reaction vessels supported in the processing zone.

In still another form, the reaction vessels are adapted to selectively contain fluids having a surface tension sufficient to support a selected head of fluid without the fluid draining through the drain openings, and the source of air at non-atmospheric pressure is adapted to selectively create a relatively lower pressure at the drain opening than at the top of the fluid to overcome the fluid surface tension and selectively drain the fluid through the drain openings.

In yet another form, the support is adapted to support the plurality of reaction vessels in at least two rows, each row having a defined space from at least one adjacent row. In a further form, the defined space between rows is a generally vertical longitudinal slot, and a bar magnet extends generally horizontally and is supported for selected vertical movement in the slot. In a still further form, the support is adapted to support the plurality of reaction vessels in at least four rows and the defined space is a generally vertical longitudinal first slot between the first and second rows and a generally vertical longitudinal second slot between the third and fourth rows, with the bar magnet being a first bar magnet supported for selected vertical movement in the first slot and a second bar magnet supported for selected vertical movement in the second slot. In a yet further form, the first and second bar magnets are supported for vertical movement together.

In still another aspect of the present invention, a method of processing analytes in fluids in reaction vessels is provided, including the steps of (1) supporting a reaction vessel containing an analyte in a fluid, the reaction vessel having a drain opening in its bottom capable of supporting a selected head of the fluid in the vessel by the surface tension of the fluid, (2) drawing the analyte to a side of the vessel to concentrate the analyte clear of the drain opening, and (3) selectively creating a pressure differential between the top of the fluid and the bottom of the drain opening sufficient to overcome the fluid surface tension and drain the fluid through the drain opening.

In one form of this aspect of the invention, the selectively creating a pressure differential step includes selectively creating a vacuum beneath the drain opening.

In another form of this aspect of the invention, the drawing step includes binding the analyte to a magnetic particle, and introducing a magnetic field into the vessel which draws the magnetic particle and bound analyte to the side of the vessel. In a further form, the magnetic field is moved vertically along the height of the reaction vessel to draw the magnetic particles and bound analyte together into a pellet in the reaction vessel. In a still further form, the moving step moves the magnetic field down from an upper position near the top of the fluid in the reaction vessel to a position near the bottom of the reaction vessel whereby the pellet is formed near a bottom side of the reaction vessel.

In yet another aspect of the present invention, a processing zone for a specimen handling device is provided, including a support adapted to support a reaction vessel in a generally vertical orientation, and a magnet supported for selected vertical movement along one side of a supported reaction vessel.

In one form of this aspect of the invention, the support is adapted to support a plurality of reaction vessels in at least two rows where each row has a defined spacing from at least one adjacent row, and the magnet extends generally horizontally and is supported for selected vertical movement in the defined spacing. In a further form, the defined spacing between rows comprises a generally vertical longitudinal slot, and magnet is a bar magnet or an electromagnet. In a still further form, (1) the support is adapted to support the plurality of reaction vessels in generally parallel first, second, third and fourth rows, (2) the defined space is a generally vertical longitudinal first slot between the first and second rows and a generally vertical longitudinal second slot between the third and fourth rows, and (3) the bar magnet includes a first bar magnet supported for selected vertical movement in the first slot and a second bar magnet supported for selected vertical movement in the second slot. In a yet further form, the first and second bar magnets are supported for vertical movement together.

In yet another aspect of the present invention, a method of processing analytes in fluids in reaction vessels is provided, including the steps of (1) supporting a reaction vessel containing an analyte in a fluid, (2) binding the analyte to a magnetic particle, (3) introducing a magnetic field into the vessel which draws the magnetic particle and bound analyte to the side of the vessel, and (4) moving the magnetic field vertically along the height of the reaction vessel to draw the magnetic particle and bound analyte together into a pellet in the reaction vessel.

In one form of this aspect of the invention, the moving step moves the magnetic field down from an upper position near the top of the fluid in the reaction vessel to a position near the bottom of the reaction vessel whereby the pellet is formed near a bottom side of the reaction vessel.

In a still further aspect of the present invention, a fluid handling mechanism is provided for an analyte testing device which includes a deck with a processing zone having a plurality of reaction vessels supported therein with upwardly facing openings. The fluid handling mechanism includes a first bulk supply of a first fluid, and a dispensing head having X discharge openings selectively positionable with each of the discharge openings over the upwardly facing openings of X selected reaction vessels, wherein X is at least four. A metering pump mechanism is adapted to selectively meter X units of a selected quantity of fluid from the first bulk supply, and selectively pump X units of metered selected quantities of fluid through the discharge openings to the selected reaction vessels.

In one form of this aspect of the invention, the deck supports a plurality of reaction vessels in a repeating pattern, each pattern including X reaction vessels, and the dispensing head discharge openings are arranged in the pattern. In a further form, the repeating pattern comprises a plurality of rows of reaction vessels. In a still further form, the rows include at least eight reaction vessels, and X is at least eight.

In another form of this aspect of the invention, a second bulk supply of a second fluid is provided, and the metering pump mechanism is adapted to selectively meter the X units of the selected quantity of fluid from a selected one of the first and second bulk supplies. In a further form, the metering pump mechanism includes X piston pumps, and X valve structures are also provided, where each valve structure is associated with one of the piston pumps and selectively switchable between providing a connection to (1) a selected one of the first and second bulk supplies, and (2) an associated discharge opening.

DETAILED DESCRIPTION OF THE INVENTION

Figure 1:
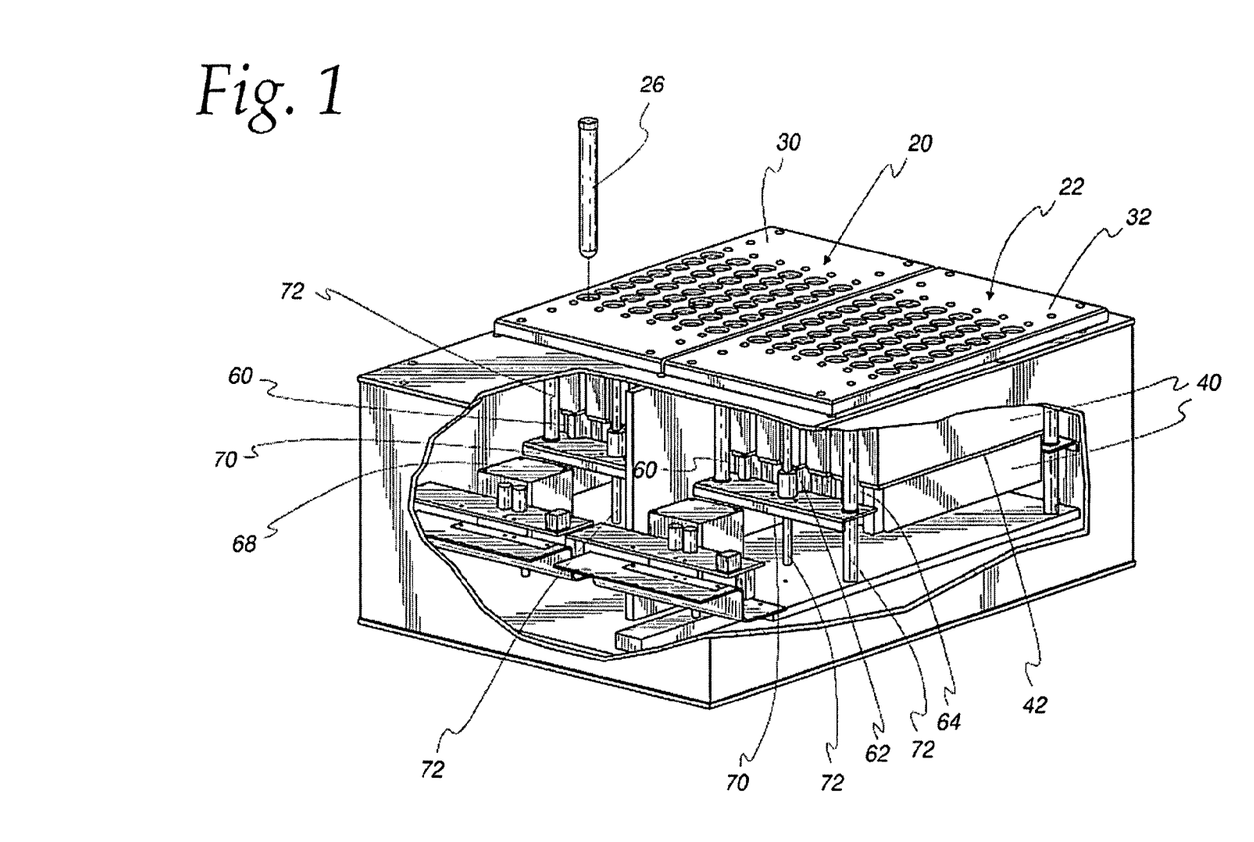
FIG. 1 is a perspective view of a processing zone and one reaction vessel according to various aspects of the present invention.

Two processing zones 20, 22 in accordance with the present invention and usable with a suitable automated testing device (not shown) are illustrated in FIG. 1. For simplicity of explanation of the invention, the overall testing device is not (and need not be) shown in the figures. For example, a suitable automatic testing device may be adapted for the substantial isolation of nucleic acids from biological samples, including the isolation and testing of nucleic acids from biological samples.

In a suitable automated testing device for such a use, for example, a hood may be provided to protect against contamination from the environment in which the zones 20, 22 are located to prevent outside contaminants from entering therein as is known in the art. Such an automatic testing device may advantageously also include one or more of the following features: (1) a receptacle to hold and segregate from samples and reagents used pipette tips such that contamination from used tips is minimized, (2) aerosol control devices, for example without limitation, (a) a sample tube or reagent tube sealer, (b) electrodes for treating surfaces and/or liquids with electrical current capable of modifying nucleic acids, (c) an ultraviolet light source capable of degrading or modifying nucleic acids, (d) an apparatus for causing laminar air flow in or around the automatic testing device, and (3) an optical detector (e.g., a flourometer) for measuring the light absorbance or fluorescence of processed samples. Tecan AG manufactures a general purpose laboratory pipetting instrument with which the various described aspects of the invention may be used. However, it should be understood that many features of such instruments, though usable with the present invention, do not form a part of the invention, and therefore are not shown in the figures. Those skilled in the art who obtain an understanding of the present invention will recognize such features, such as disclosed in, for example, in U.S. Ser. No. 10/360,956 titled "Apparatus and Method for Handling Fluids for Analysis", filed Feb. 7, 2003, U.S. Pat. No. 6,413,780, titled "Structure and Method for Performing a Determination of an Item of Interest in a Sample", and U.S. Publication No.

2002-0127727 also titled "Structure and Method for Performing a Determination of an Item of Interest in a Sample", the complete disclosures of which are hereby incorporated by reference.

Further, a plurality of processing zones may be used with a single testing device such as shown, including not only multiple processing zones 20, 22 embodying aspects of the present invention such as shown in FIG. 1, but also additional processing zones (not shown) for different types of processing or specimen handling. For example, additional handling zones can be provided wherein reaction vessels may be prepared prior to desired processing by adding specimens, etc. The multiple processing zones 20, 22 illustrated in FIG. 1 assist in minimizing resource contention (i.e., conflicts arising where processing using one group of reaction vessels may be delayed until another group of reaction vessels has completed processing at the next required processing zone 20.

FIG. 1 generally illustrates a processing zone 20 at which testing of specimen samples may be done. In suitable testing devices with which the processing zones 20, 22 as discussed herein may be used, reaction vessels 26 (only one of which is shown in FIG. 1) containing specimens for testing may be loaded onto supports 30, 32 at each zone 20, 22. The supports 30, 32 may be support brackets or racks, for example, defining rows in which reaction vessels 26 may be supported, each with an upwardly open top. The supports 30, 32 may serve as heat shields to protect a user from heat blocks therebeneath (as described below). Suitable movable carriers may also be used which are transportable to and from the processing zones 20, 22 (e.g., manually or by a suitable robotic arm) to facilitate handling reaction vessels where desired.

The supports 30, 32 illustrated in FIG. 1 will support reaction vessels 26 in a repeating pattern, with a pattern consisting of a row of eight reaction vessels 26 repeated six times, whereby a total of forty-eight reaction vessels 26 may be processed simultaneously at one processing zone 20 or 22. Thus, in the present description, the processing may be to isolate analytes of interest from up to forty-eight specimens (e.g., DNA or RNA), after which processing the isolated analyte may be further tested according to an appropriate protocol. However, it should be understood that the present invention is not limited in any way to such processing, and could as readily be used with a device in which different processing or protocols are carried out.

In the illustrated embodiment, each of the processing zones 20, 22 includes heat blocks 40 which may be suitably controlled to heat the reaction vessels 26 to whatever temperatures, for whatever periods of time, is required by the processing or protocol being carried out. The heat blocks 40 may be configured so as to surround the reaction vessels 26 to dissipate heat from a suitable heater 42 evenly throughout the reaction vessels 26 in the processing zone 20, 22.

Figures 2A, 2B, 2C:
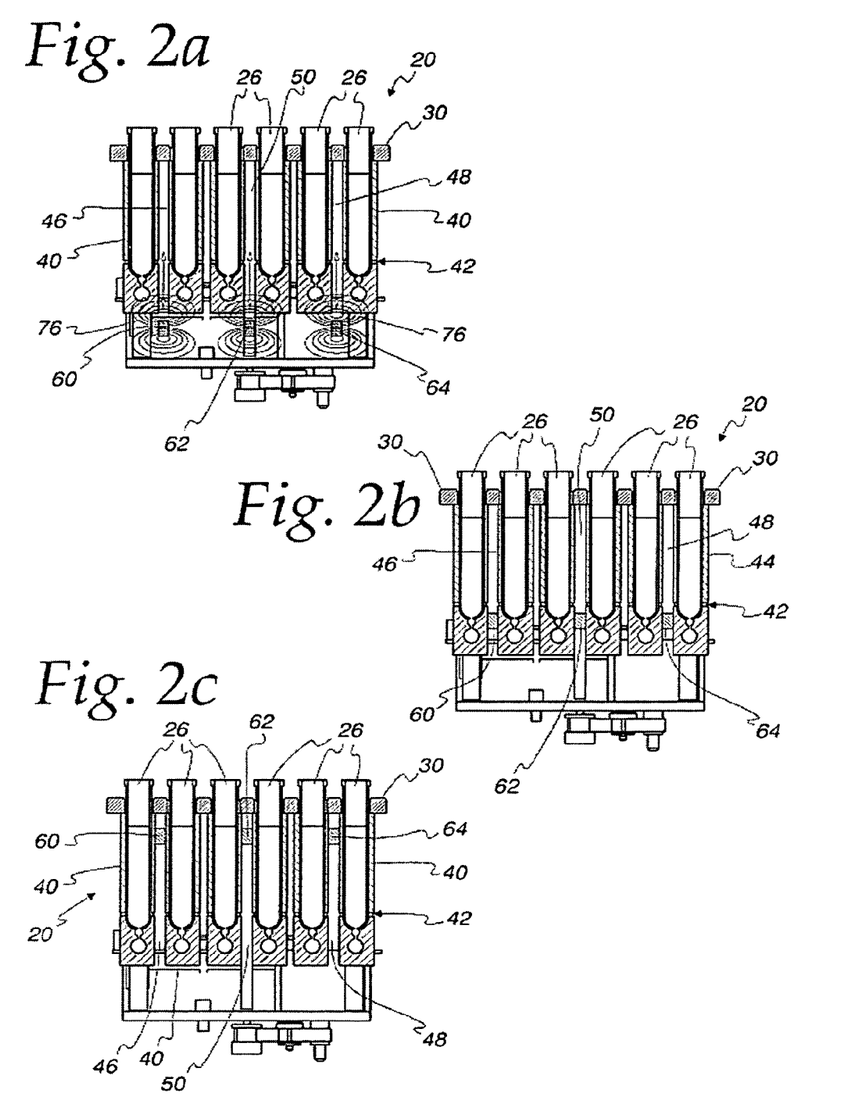
FIGS. 2a, 2b, and 2c are cross-sectional views of a processing zone supporting a plurality of reaction vessels illustrating the magnets in different positions according to one aspect of the present invention.

The heat blocks 40 may also be arranged with a longitudinal, vertical slot between adjacent rows of reaction vessels 26. For example, as illustrated in FIGS. 2a-2c, there is a slot 46 between the left two rows of vessels 26, a slot 48 between the right two rows of vessels 26, and a slot 50 between the middle two rows of vessels 26.

In accordance with one aspect of the invention, suitable bar magnets 60, 62, 64 may be supported for movement in the slots 46, 48, 50 between the rows of reaction vessels 26. The bar magnets 60, 62, 64 are suitably supported for selected vertical movement together in the slots 46, 48, 50, as by a controlled drive 68 which moves a cross-support 70 on vertical guide rods 72. It would, however, be within the scope of this aspect of the present invention to use any structure which would suitably control vertical movement of the bar magnets 60, 62, 64 as described hereafter so as to move the magnetic field 76 (see FIG. 2a) in the reaction vessels 26. Moreover, it would be within the scope of the present invention to use still other suitable magnets, such as electromagnets. Still further, it should be understood that it would be within the scope of some aspects of the present invention to not use magnets at all (e.g., where certain aspects of the invention are used in processing which does not magnetically separate the analytes of interest from the fluid including, as one example, non-magnetic sample preparation in which the analytes of interest are bound to silica membrane).

Specifically, during processing of a specimen within the reaction vessel 26, the analyte of interest dispersed in the reaction vessel 26 may be suitably bound to a magnetic material or particles in a suitable manner such as is known in the art. During processing thereafter, the magnets 60, 62, 64 may be selectively moved vertically in the slots 46, 48, 50 to draw the magnetic particles (and bound analyte of interest) to one side of the vessel 26. Moreover, by selectively moving the magnets 60, 62, 64 along the side of the vessels 26 in the slots, the magnetic particles and bound analyte of interest within the reaction vessel 26 may be strongly drawn to the side of the vessels 26 throughout the height of the vessel 26 by essentially subjecting the vessel contents to a uniform magnetic force throughout its height. Further, by moving the magnets 60, 62, 64 from an upper (lyse capture) position such as illustrated in FIG. 2c to a bottom (wash capture) position as illustrated in FIG. 2b, magnetic particles and bound analyte of interest may not only be drawn to the side of the vessels 26 but may also then be pulled down along the side of the vessels 26 as the magnets 60, 62, 64 move down whereby a desired pellet of such materials is formed at the bottom corner of the vessels 26.

While the above described structure using bar magnets with multiple vessels 26 may be particularly efficiently used, it should be understood that most broadly, aspects of the present invention could also include the use of a magnet as described with a single reaction vessel 26, that is, moving a magnet along one side of one vessel 26 to draw the magnetic particles and bound analyte of interest to the side of the vessel 26 and down to form a pellet at a bottom corner of the vessel 26.

Figure 3A:
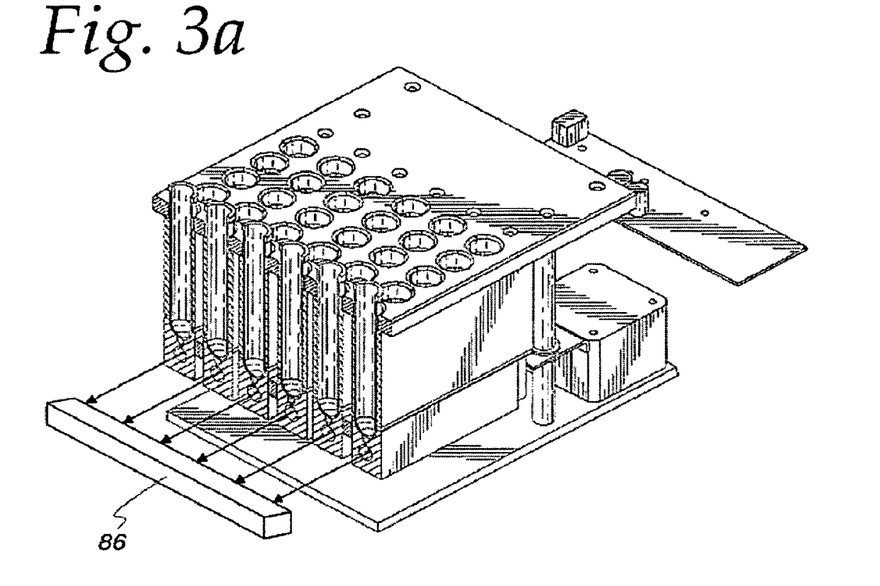
FIG. 3a is a perspective, cross-sectional view of a processing zone which includes the present invention.
Figure 3B:
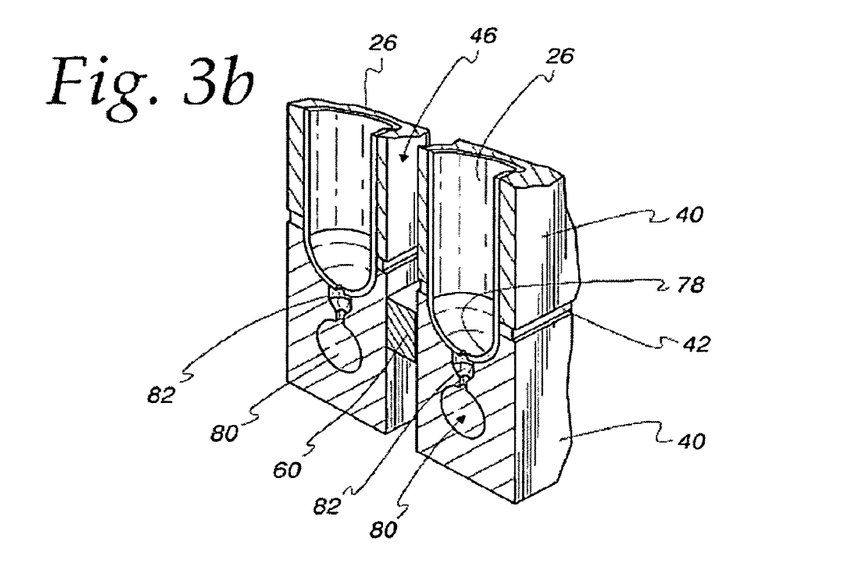
FIG. 3b is an enlarged cross-sectional partial view showing two reaction vessels supported in the processing zone.

FIGS. 3a-3b illustrate yet another aspect of the present invention. Specifically, each processing zone 20, 22 may include concave recesses 78 (see FIG. 3b) for receiving the bottoms of the reaction vessels 26, for example, in the heat blocks 40. A horizontal drain passageway or channel 80 may extend along the length of the heat blocks 40 beneath each row of vessels 26, with a vertical passageway 82 connecting the horizontal passageway 80. A suitable vacuum source (indicated schematically at 86 in FIG. 3a) may be applied to the passageways 80, 82 to selectively draw/drain fluid from the vessels 26 as described below. While a vacuum source 86 is described herein, it should be understood that the significant feature is a lower pressure beneath discharge or drain openings in the bottom of the vessels 26 (as described in detail below) relative to the pressure on the fluid at the top of the vessels 26. Therefore, it should be understood that this aspect of the invention could also be accomplished through the application, for example, of high pressure to the top of the reaction vessels 26 where the passageways 80, 82 are at atmospheric pressure, or a combination of pressure and vacuum.

Figure 4A:
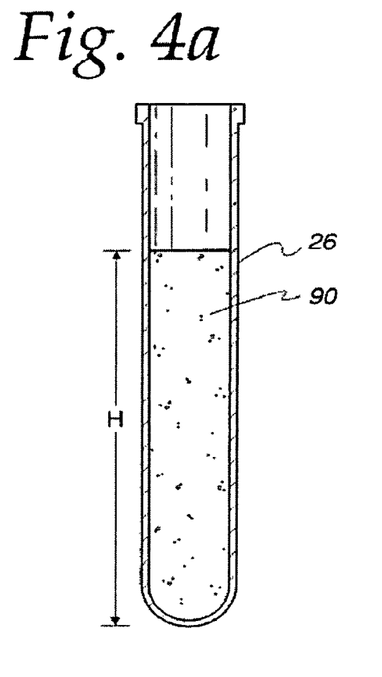
FIG. 4a is a cross-sectional view of a reaction vessel according to one aspect of the present invention.

Specifically, as illustrated in FIG. 4a, it is contemplated as an example that a reaction vessel 26 may be provided with a fluid 90 and sample having a depth (or height or head) H.

A discharge or drain opening 92 is provided in the bottom of the reaction vessel 26, where the drain opening 92 is configured so that the surface tension of the fluid 90 in its condition at the processing zone 20, 22 is sufficient to support the height of fluid without the fluid draining through the drain opening 92. It should be understood that, while a single opening 92 is shown in FIG. 4a, it would advantageously be within the scope of the present invention to define the drain opening via multiple openings through the bottom of the vessel 26.

Figure 4B:
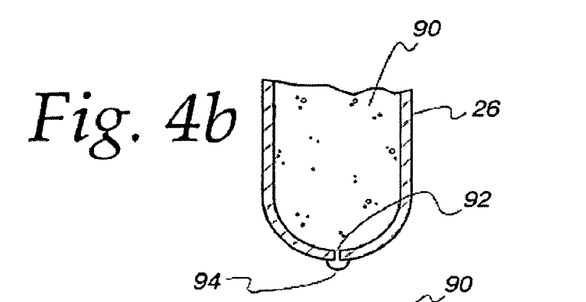
FIGS. 4b, 4c, 4d, and 4e are enlarged cross-sectional partial views of different reaction vessels incorporating one aspect of the present invention.

FIG. 4b illustrates a reaction vessel 26 with one configuration of drain opening 92, where fluid 90 has passed through the drain opening 92 so as to form a bead 94 around the opening 92. So long as the opening 92 is small enough to maintain a bead 94 which is no greater in size than the surface tension of the fluid 90 can maintain, the fluid 90 will be supported in the vessel 26 (that is, until an additional force, a relative pressure between the top and bottom of the fluid 90, is selectively created by the introduction of a vacuum in the passageways 80, 82 beneath the vessels 26).

Figure 4C:
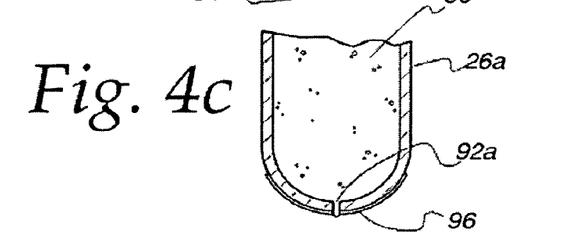

FIG. 4c discloses an alternative embodiment of a reaction vessel 26a, wherein a suitable non-wettable coating or surface 96 is provided around the drain opening 92a. Such a non-wettable coating 96 will prevent a bead from spreading out onto the coating (FIG. 4b illustrates a bead 94 which spreads out onto the outer surface of the vessel 26), such that a larger size drain opening 92a may be used while still maintaining the ability of the surface tension of the fluid 90 to support a desired height of fluid 90 in the vessel 26a.

Figure 4D:
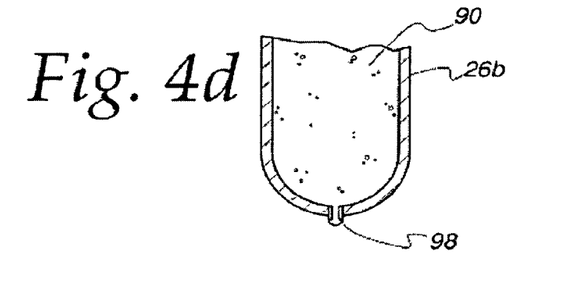

FIG. 4d discloses still another embodiment of a reaction vessel 26b, wherein a protruding tube or flange 98 is provided around the drain opening 92b. The flange 98 may also prevent the bead from spreading out to an area much larger than the flange 98, thereby allowing use of a larger drain opening 92b while still maintaining the ability of the surface tension of the fluid 90 to support the fluid 90 as described for FIG. 4c.

Figure 4E:
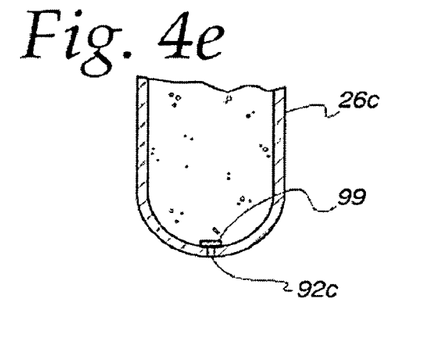

FIG. 4e discloses yet another embodiment of a reaction vessel 26c, in which a hydrophobic frit 99 or other suitable hydrophobic porous material (such as may be obtained from Porex Corporation of Fairburn, Ga.) is associated with the vessel 26c to define the drain opening 92c. The hydrophobic frit 99 may be advantageously selected, based on the fluid, whereby the frit 99 will support the desired height of fluid 90 in vessel 26c, and will allow the fluid to pass therethrough when a selected pressure differential is introduced between the top of the vessel 26c and beneath the frit 99/drain opening 92c. Thus, where a fluid having low surface tension properties is used (e.g., alcohol), the porosity of the frit material may advantageously be less than the material used with fluids having higher surface tension properties to enable the desired height of fluid to be supported as desired.

The above described vessels 26, 26a, 26b, 26c are particularly advantageous inasmuch as such vessels are low cost disposables. However, it should be understood that aspects of the present invention encompass still further vessels having drain openings which will support a head of fluid 90 by other than the fluid surface tension, while allowing that fluid to be selectively drained from the vessel responsive to a selected pressure differential created (e.g., by the introduction of a vacuum in the passageways 80, 82 beneath the vessels 26).

Figure 4F:
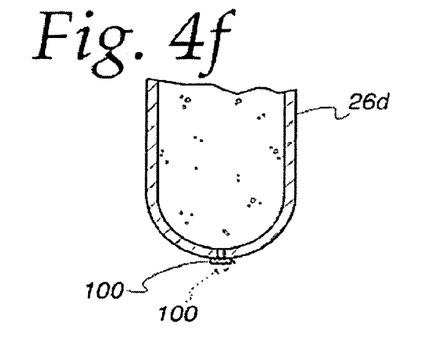
FIG. 4f is an enlarged cross-sectional partial view of a reaction vessel used with a passive valve as usable with certain aspects of the present invention.

For example, a drain opening consisting of not only an opening in the vessel 26 but also a suitable passive valve may be provided to provide the desired fluid flow, where the passive valve is biased to block fluid flow unless a selected pressure differential across the valve is created. FIG. 4f illustrates a reaction vessel 26d having a duckbill valve 100 as one example of a suitable valve which would be pulled open by a selected pressure differential resulting from a vacuum in the passageways 80, 82. Those skilled in the art will recognize that many other valve structures providing such operation would be suitable, including, for example, umbrella valves, flapper valves and spring biased ball check valves, and could also be advantageously used with certain aspects of the present invention.

Figure 4G:
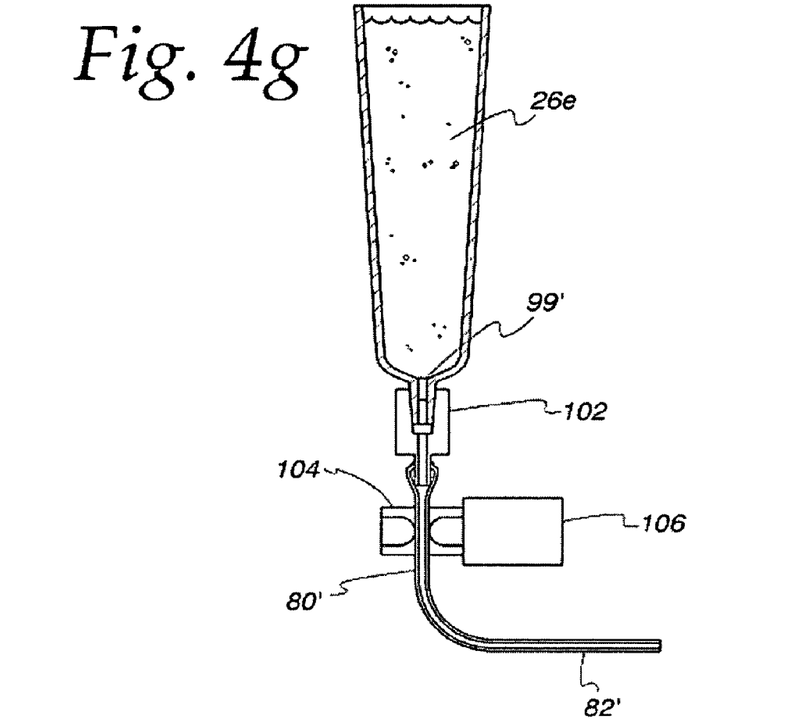
FIG. 4g is an enlarged cross-sectional partial view of a reaction vessel used with an active valve as usable with certain aspects of the present invention.

Active valves may also be advantageously used with certain aspects of the present invention. FIG. 4g illustrates a reaction vessel 26e with a suitable connection 102 to passageways 80', 82' with a suitable pinch valve 104 and suitable control 106 for selectively closing and opening the passageway 80' as desired for operation. A hydrophobic frit 99' may also be provided in the bottom opening of the vessel 26e. Active valves may advantageously be selected which will support the desired height of fluid and may be opened to allow fluid to drain from the vessel 26e without assist by a pressure differential. However, it would be within the scope of certain aspects of the present invention to additionally provide a vacuum to assist in such draining when the active valves 104 are open.

Valves such as described above may be a part of the reaction vessel, or part of the vacuum passageways 80, 82 beneath the vessel.

Figure 5:
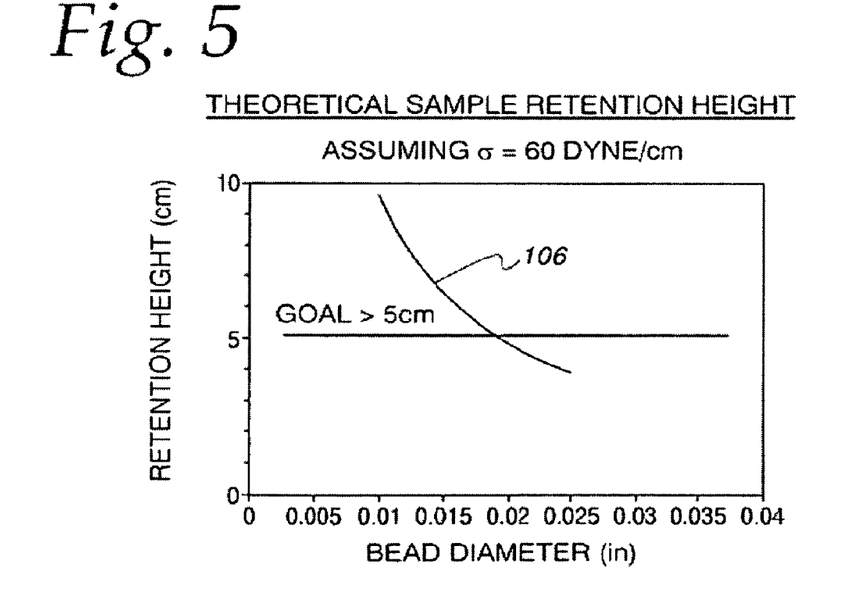
FIG. 5 is a graph showing the theoretical head or height of a particular fluid which will be retained based on the diameter of the fluid bead at the drain opening.

FIG. 5 illustrates a theoretical retention height H of the following fluid 90, such as may be commonly encountered as one example:

| | |
|---|---|
| Vessel Content | 1 mL Plasma + 2.5 mL Buffer Solution |
| Sample height | 5 cm |
| Temperature | 50 degrees C. |
| Sample density $\rho$ | 1 g/cc |
| Sample surface tension $\sigma$ | 60 dyne/cm (est. at 50 degrees C.) |
| Sample viscosity $\mu$ | 0.87 cP (est. at 50 degrees C.) |

As can be seen from the curve 106 in FIG. 5, for such a fluid, the 60 dyne/cm surface tension would be sufficient to support a height H of fluid of 5 cm if the bead diameter is slightly less than 0.02 inches (or smaller). Thus, any drain opening 92 which will form a bead diameter no larger than slightly less than 0.02 inches will be able to retain the fluid 90 in the reaction vessel 26 until a relative pressure is introduced via the vacuum 86.

Figure 6:
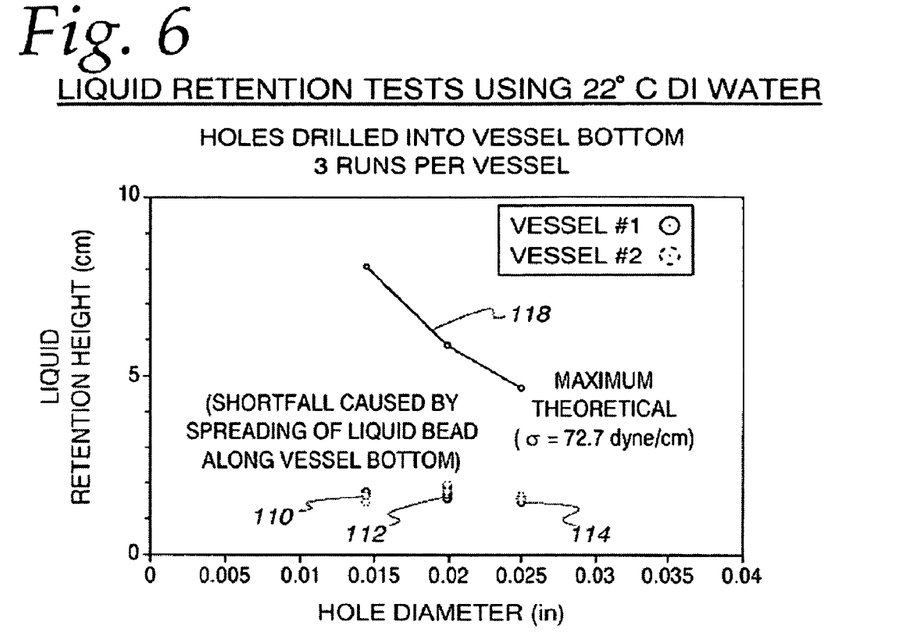
FIG. 6 is a graph illustrating test results of the head or height of a particular fluid which will be retained in a reaction vessel having different hole diameters.

As illustrated in FIGS. 4b and 6, however, the drain opening 92 as in FIG. 4b may not be as large as the allowable bead size inasmuch as the bead may tend to spread out around the opening 92. FIG. 6 shows the results 110, 112, 114 of tests using DI water at 22 degrees C. (with a surface tension a of 72.7 dyne/cm), in which it can be seen that the actual height of supported liquid 90 (generally around 1 to 2 cm) for a given hole diameter was far below the maximum theoretical liquid retention height 118 for a bead of such water having that same diameter. Such a shortfall can be attributed in large part to the spreading of the bead (see 94 in FIG. 4b) around the opening 92. As previously discussed, the FIGS. 4c and 4d embodiments address this issue by limiting the spreading of the bead around the opening 92a, 92b.

Figure 7:
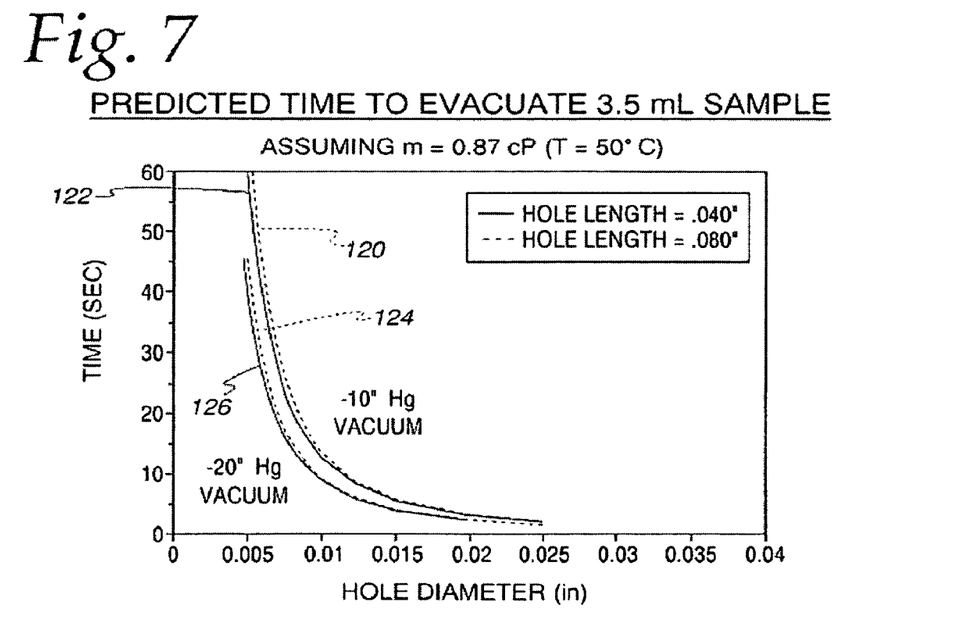
FIG. 7 is a graph illustrating the predicted time required to evacuate a 3.5 mL sample through different drain openings.

FIG. 7 illustrates the predicted time to evacuate a 3.5 mL sample (e.g., a 5 cm fluid height from a conventional reaction vessel 26) based on the hole diameter. Different theoretical conditions are illustrated using the FIG. 5 sample fluid (having a fluid viscosity $\mu$ of 0.87 cP at a temperature of 50 degrees C.). Hole lengths of 0.040 inch and 0.080 inch, and vacuum of −10 inches Hg and −20 inches Hg, are illustrated. Specifically, the theoretical evacuation time for a hole length of 0.080 inch using a −10 inch Hg vacuum is shown at 120, the theoretical evacuation time for a hole length of 0.040 inch using a −10 inch Hg vacuum is shown at 122, the theoretical evacuation time for a hole length of 0.080 inch using a −20 inch Hg vacuum is shown at 124, and the theoretical evacuation time for a hole length of 0.040 inch using a −20 inch Hg vacuum is shown at 126.

As can be seen from the FIG. 7 curves 120, 122, 124, 126, the hole length has a theoretical minor impact on the predicted evacuation time. The amount of vacuum assist has a greater impact on the time, but that is still relatively small. Of particular significance is the indication that hole diameters which are about 0.01 inch or smaller will have significantly greater evacuation times, with holes much smaller than about 0.005 inch theoretically incapable of evacuating the fluid with the indicated vacuum levels. Since evacuation time could thus potentially significantly slow processing of samples, it should be appreciated that the larger hole diameters above 0.01 inch would provide advantageous speeding of processing over smaller hole diameters. Thus, the FIGS. 4c and 4d embodiments, for example, which will enable the reaction vessels 26a, 26b to retain the desired height of fluid 90 with larger size drain openings 92a, 92b such as previously described, may be particularly advantageously used with the present invention.

This manner of draining fluid 90 from the reaction vessels 26 should thus be appreciated to be fast and convenient. Further, it should be appreciated that such draining may be accomplished with minimal cost of disposable pipettes. Moreover, it should be appreciated that the use of reaction vessels 26 with bottom drain openings 92 such as described may be advantageously used with the previously described movable magnets 60, 62, 64, inasmuch as the magnets 60, 62, 64 operate to pull the magnetic particles and bound analyte of interest to the bottom side of the vessel 26, whereby the pellet of such material will be clear of the drain opening 92.

Figure 8:
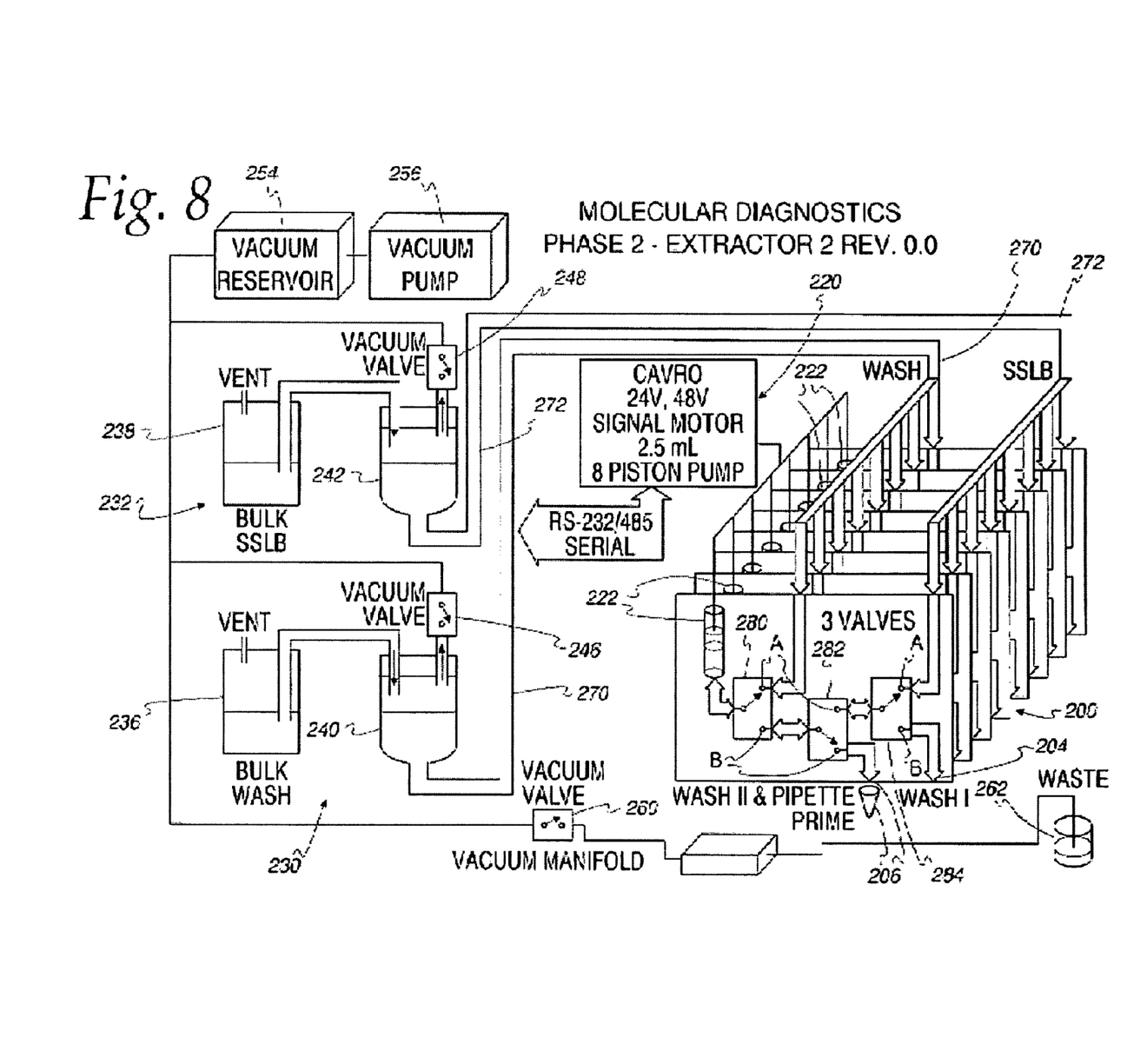
FIG. 8 is a diagram of a fluid handling mechanism according to an aspect of the present invention.

FIG. 8 discloses a further aspect of the present invention, which uses a traveling head 200 connected to bulk supplies of fluid, whereby desired amounts of such fluids may be added to sets of vessels 26 (not shown in FIG. 8).

Specifically, the head 200 includes two sets of outlets 204, 206, with one outlet set 204, for example, used for wash, and a second outlet set 206 used for wash and pipette prime. A second (or additional) outlet set 206 may be provided, for example, where a different type of discharge (e.g., a spray nozzle) may be desired. In the illustrated embodiment, the outlet sets 204, 206 include eight outlets arranged in a row to match the pattern of the vessels 26 supported in the processing zones 20, 22. Thus, the head 200 may be arranged above any selected pattern row of eight vessels 26 in a processing zone 20, 22 whereby the eight outlets of a selected set 204, 206 will be aligned above the selected eight vessels 26 so that fluid discharged from the head outlets will enter the selected vessels 26.

Associated with the head 200 is a suitable pump 220 which may meter desired amounts of selected fluids (as further described below) for each of the outlets in a set 204, 206. One such suitable metering pump 220 is illustrated in FIG. 8 as a Cavro 24V, 48V signal motor which includes eight 2.5 mL piston pumps 222. Cavro Scientific Instruments Inc. is located at 2450 Zanker Road, San Jose, Calif., USA 95131. As described further herein, this pump 220 will meter a desired amount (e.g., 2.5 mL) of fluid from the bulk supplies for each of the X number (eight in the illustrated embodiment) outlets of each outlet set 204, 206. However, it should be understood that the details of this pump 220 do not form a part of the invention, and any pump and valving system which will meter a selected number (X, e.g., eight) of a selected quantity (e.g., 2.5 mL) of fluid for discharge through the outlets of a selected outlet set 204, 206 would be suitable.

Suitable bulk supplies 230, 232 may be provided according to the expected needs of the testing. In the illustrated example, there is a bulk supply 230 of wash and a bulk supply 230 of single step lysis buffer (SSLB). As illustrated in FIG. 8, each bulk supply 230, 232 may include a refillable tank 236, 238 which is connected to a sealed dispensing tank 240, 242. A valve 246, 248 may selectively connect the dispensing tank 240, 242 to a vacuum source (vacuum reservoir 254 and vacuum pump 256) to assist in maintaining a desired level of fluid in the dispensing tank 236, 238, and to permit fluid to be drawn off the top of the dispensing tanks 240, 242 if desired. Another vacuum valve 260 may be used to selectively draw such materials to a waste container 262. It should be understood, however, that the illustrated bulk supply structure is merely one suitable example of a structure which may be used with this aspect of the invention, and any suitable bulk supply from which the needed fluids may be pumped by the metering pump 220 may be used with this aspect of the present invention.

The dispensing tanks 236, 238 are suitably connected to the traveling head 200, as by flexible hoses 270, 272.

A suitable valve structure is provided to enable the metering pump 220 to be selectively connected to the bulk supply of selected fluid in order to obtain X (e.g., eight) units of selected quantity (e.g., 2.5 mL), after which the X units of selected fluid may be sent to a selected set of outlets 204, 206 for discharge into a selected set of reaction vessels 26 over which the head 200 has positioned the selected outlet set 204, 206.

One valve structure which would be suitable for a head 200 connected to two bulk supplies 236, 238 and having two outlet sets 204, 206 is the three-valve structure illustrated in FIG. 8. One such valve structure is associated with each of the piston pumps 222 illustrated. While the illustrated embodiment may be advantageously used with this aspect of the invention, it should be recognized that this aspect of the invention may be readily practiced with different valve structures.

Specifically, the illustrated three-valve structure includes valves 280, 282, 284, each of which may be selectively switched between path A and path B. During a single cycle, for example, valve 280 may be connected to path A, after which the metering pump 220 may be activated to draw 2.5 mL of wash fluid from bulk supply 230 through hose 270 into the piston pumps 222. Valve 280 may then be switched to path B, valve 282 switched to path A, and valve 284 switched to path B, whereby the piston pumps 222 may then be operated to discharge the eight 2.5 mL units of wash fluid through the eight outlets of outlet set 284 into vessels 26 (not shown) located beneath those outlets.

When used with a processing zone 20, 22 in which there are six rows of eight reaction vessels 26 such as previously described, the above process may be repeated six times to provide the wash fluid to all forty-eight reaction vessels 26.

After the wash fluid has been discharged into all of the selected reaction vessels 26, operation of the valve structure can be changed to supply a different fluid if needed based on the testing being accomplished. For example, if SSLB fluid is thereafter desired, valve 280 positioned at path B, valve 282 positioned at path A, and valve 284 positioned at path A, whereby the piston pumps 222 may then be operated to draw 2.5 mL of SSLB fluid from bulk supply 232 through hose 272 into the piston pumps 222. Then, valve 280 may be kept at path B and valve 282 switched to path B, whereby the piston pumps 222 may then be operated to discharge the eight 2.5 mL units of SSLB fluid through the eight outlets of outlet set 284 into vessels 26 (not shown) located beneath those outlets. This processing may then be repeated as necessary to provide SSLB fluid to all of the selected reaction vessels 26.

It should be appreciated that the FIG. 8 aspect of the invention will enable the processing zones 20, 22 to be used efficiently and reliably. The desired amounts of fluid may be easily and reliably metered in the desired amounts. Further, this may be accomplished quickly, without the delay time which would be required by a dispensing head which travels back and forth from the processing zones and bulk supplies each time a set of reaction vessels requires such fluids.

It should also be appreciated that the various aspects of the invention described herein may be combined to provide a processing zone which may be advantageously operated to efficiently and quickly process samples.

Still other aspects, objects, and advantages of the present invention can be obtained from a study of the specification, the drawings, and the appended claims. It should be understood, however, that the present invention could be used in alternate forms where less than all of the objects and advantages of the present invention and preferred embodiment as described above would be obtained.

What is claimed is:

1. A processing zone for a specimen handling device, said processing zone comprising (a) a support for a plurality of reaction vessels, each reaction vessel having a drain opening in its bottom, said drain opening being adapted such that a selected head of fluid can be supported in the reaction vessel; (b) passages adapted to communicate with the drain openings of the reaction vessels when they are supported in the support; and (c) a source of air at non-atmospheric pressure adapted to selectively drain fluid through the drain openings in the reaction vessels when they are supported in the support, wherein said support is adapted to support the plurality of reaction vessels in at least two rows, each row having a defined space from at least one adjacent row, wherein said defined space between said at least two rows comprises a generally vertical longitudinal slot; said processing zone further comprising a magnet extending generally horizontally and supported for selected vertical movement in said slot.

2. The processing zone of claim 1, wherein said source of air at non-atmospheric pressure is a vacuum source for drawing a vacuum in said passages.

3. The processing zone of claim 1, further comprising a heater for heating reaction vessels supported in said processing zone.

4. The processing zone of claim 1, wherein said reaction vessels are adapted to selectively contain fluids having a surface tension sufficient to support a selected head of fluid without the fluid draining through said drain openings, and said source of air at non-atmospheric pressure is adapted to selectively create a relatively lower pressure at the drain opening than at the top of the fluid to overcome said fluid surface tension and selectively drain the fluid through the drain openings.

5. The processing zone of claim 1, wherein said support is adapted to support the plurality of reaction vessels in at least four rows and said defined space comprises a generally vertical longitudinal first slot between the first and second rows and a generally vertical longitudinal second slot between the third and fourth rows, and said magnet comprises a first bar magnet supported for selected vertical movement in the first slot and a second bar magnet supported for selected vertical movement in the second slot.

6. The processing zone of claim 5, wherein said first and second bar magnets are supported for vertical movement together.

* * * * *